United States Patent
Manneck

(10) Patent No.: US 8,025,704 B2
(45) Date of Patent: Sep. 27, 2011

(54) MATTING ADDITIVE FOR BLOND HAIR DYEING

(75) Inventor: Hartmut Manneck, Klein Wesenberg (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 13/022,726

(22) Filed: Feb. 8, 2011

(65) Prior Publication Data
US 2011/0126361 A1    Jun. 2, 2011

Related U.S. Application Data

(63) Continuation of application No. PCT/EP2009/057013, filed on Jun. 8, 2009.

(30) Foreign Application Priority Data

Aug. 8, 2008 (DE) .......................... 10 2008 036 957

(51) Int. Cl.
*A61Q 5/10* (2006.01)

(52) U.S. Cl. ............. 8/405; 8/426; 8/435; 8/462; 8/465; 8/576; 8/579; 8/640; 8/643; 8/657; 8/673; 132/202; 132/208

(58) Field of Classification Search ............. 8/405, 426, 8/435, 462, 465, 576, 579, 640, 643, 657, 8/673; 132/202, 208
See application file for complete search history.

(56) References Cited

U.S. PATENT DOCUMENTS

| 7,189,265 B2 * | 3/2007 | Said et al. .......................... 8/405 |
| 2004/0143910 A1 | 7/2004 | Said et al. |
| 2005/0196367 A1 | 9/2005 | Ohta et al. |
| 2005/0257328 A1 | 11/2005 | Sallwey et al. |

FOREIGN PATENT DOCUMENTS

| CA | 2613049 A1 | 4/2008 |
| DE | 19745293 | 4/1999 |
| EP | 1759684 A1 | 3/2007 |
| WO | 9213829 A1 | 8/1992 |

OTHER PUBLICATIONS

STIC Search Report dated May 4, 2011.*
Schrader, Karlheinz. Grundlagen und Rezepturen der Kosmetika (Fundamentals and Formulations of Cosmetics), 2, Hüthig Buch Verlag GmbH, Heidelberg 1989.
Römp-Lexikon. Chemie. George Thieme Verlag, vol. 10, 1997, pp. 1764.
Umbach, W. Kosmetik Entwicklung, Herstellung und Anwendung kosmetischer Mittel, Georg Thieme Verlag, 1995.

* cited by examiner

*Primary Examiner* — Eisa Elhilo
(74) *Attorney, Agent, or Firm* — David P. LeCroy

(57) ABSTRACT

Agent having at least one non-ionic component having an HLB of 8.0 or less are disclosed, as well as the combination of a blue and red substantive dye wherein the weight ratio of the blue dyes as opposed to the red dyes is 1 or greater. Further disclosed are agents for dyeing human hair blond having at least one oxidizing agent preparation and optionally a bleaching force reinforcing preparation. The agents make it possible to avoid undesired color shifts towards yellow or red nuances during blond hair dyeing.

12 Claims, No Drawings

MATTING ADDITIVE FOR BLOND HAIR DYEING

CROSS REFERENCE TO RELATED APPLICATIONS

The present application is a continuation of International Patent Application No. PCT/EP2009/057013 filed 8 Jun. 2009, which claims priority to German Patent Application No. 10 2008 036 957.8 filed 8 Aug. 2008, both of which are incorporated herein by reference.

The subject matter of the present application concerns matting additives for blonding keratinic fibers, especially human hair, as well as agents for blonding keratinic fibers without incurring unwanted color shifts into yellow to reddish nuances. Furthermore, a method for preparing the agent and process for blonding keratinic fibers without unwanted color shifting by employing the agent according to the invention are described.

Modifying the shape and color of hair represents an important area of modem cosmetics. This allows the appearance of hair to be matched to both actual fashion trends and the individual wishes of each person. Permanent sets and other methods for changing the shape of hair can be employed for this, nearly independently of the type of hair to be treated. In contrast, dyeing, especially blond-dyeing or blonding methods, are limited to certain initial hair colors. Thus, basically only dark blond or light hair is suitable for lightening methods—referred to as blonding methods. There still exists a need for effective methods, especially for dyeing darker hair colors blond. Principles of the blonding method are known to one skilled in the art and are reviewed in relevant monographs such as K. Schrader, Grundlagen and Rezepturen der Kosmetika, $2^{nd}$ Ed. (1989), Dr. Alfred Hüthig Verlag, Heidelberg, or W. Umbach (Editor), Kosmetik, $2^{nd}$ Ed. (1995), Georg Thieme Verlag, Stuttgart, N.Y.

For dyeing human hair blond, solid or pasty preparations with solid oxidizing agents are usually blended with a dilute solution of hydrogen peroxide immediately prior to the application. This mixture is then applied to the hair and rinsed out again after a defined contact time. The contact time on the hair for obtaining complete coloration lightening can range from 30 to 60 minutes. It is obvious to users of this blonding agent that there is a need to decrease contact time.

In order to achieve an adequate blonding effect, such agents are usually strongly alkaline, with pH being in the range from 9 to 10.5. Such high pH values are required in order to ensure that the external squamosal layer (cuticula) opens, thereby enabling the active species (hydrogen peroxide) to penetrate into the hair. Ammonia is normally employed as the alkalizing agent, but ammonia has the known disadvantages of an unpleasant smell and possible irritation.

In the past, alternative alkalizing agents were often also used and indeed, when mixed with ammonia, yielded acceptable blonding power; however, they could not completely replace ammonia. Consequently, it is still desirable to reduce the ammonia concentration without compromising the blonding power of the agent.

In order to achieve large color differences in the bleaching process (e.g., in particular for decolorizing dark or black hair), bleach activators such as persalts are often required as additional peroxide sources in addition to the already mentioned hydrogen peroxide preparations, and/or carbonates as an additional alkalizing agent.

Therefore, dyeing dark hair color blond represents a particular challenge. The natural hair color is determined by melanin in the cortex of the hair fiber, wherein the ratio of the two classes of pigments, eumelanin with brownish black tints and pheomelanin with reddish orange tints, determines the actual hair color. In the blonding process, the natural melanin colorants are typically destroyed oxidatively so that the fibers become decolorized. However, due to the different oxidative decomposition rates of the various classes of melanin pigments, the hair is not uniformly decolorized. In darker fibers with high melanin content there often remains a certain fraction of pigments, reflected by yellowish to reddish nuances. Consequently, a color shift towards warmer tints occurs especially when dyeing darker hair blond. Such color shifts towards warmer tints are usually not wanted by the user. According to the science of coloration, this color shift is consequently mostly counteracted by a tint with the corresponding complementary color. The aim here is a cooler silvery impression of the bleaching result. In this context, the term "matting" is used by one skilled in the art. Depending on the initial hair color, a suitable mixture of tinting agents must be used in order to compensate correspondingly more reddish color shifts by more greenish tinting agents or more yellowish color shifts by if anything violet tinting agents.

Tinting agents typically employed are often not sufficiently stable under the aggressive conditions of the lightening preparation (e.g., strong oxidizing agents, high pH). Thus, the blonding step and tinting step must usually be carried out sequentially. However, a one-step blonding that already has the matting color compensation for the unwanted warm tints is particularly advantageous for reasons of user comfort. Accordingly, there exists a need for blonding agents that, by the addition of stable tinting components into the application preparation, achieve a good color compensation and thereby a high matting.

It has now been surprisingly found that the mixture of red and blue substantive dyes in a certain weight ratio in combination with a non-ionic component having an HLB of 8.0 or less is extremely suitable as a stable matting additive for blonding agents and/or lightening agents for keratinic fibers, especially human hair.

Consequently, a first subject matter of the present invention is an agent comprising in a cosmetic carrier at least one non-ionic component having an HLB value of 8.0 or less, the agent additionally comprising a combination of at least one blue substantive dye and one red substantive dye wherein the value of the weight ratio between the sum of all blue substantive dyes and the sum of all red substantive dyes is 1 or greater.

Keratin-containing or keratinic fibers are inventively understood to mean furs, wool, feathers and in particular human hair. Although the present agents are primarily suitable for dyeing and/or lightening keratin-containing fibers, still nothing prevents their use in other fields.

Agents according to the invention comprise the active substances in a cosmetic carrier. In the context of the invention, the cosmetic carrier is aqueous, alcoholic or aqueous-alcoholic. For the purposes of dyeing hair, such carriers include creams, emulsions, gels and also surfactant-containing foaming solutions, such as shampoos, foam aerosols or other preparations suitable for use on hair. For the purposes of the present invention, aqueous-alcoholic carriers are understood to mean water-containing solutions comprising 3 to 70% by weight of a $C_1$-$C_4$ alcohol, particularly ethanol or isopropanol. Agents according to the invention can also comprise further organic solvents such as 4-methoxybutanol, ethyl diglycol, 1,2-propylene glycol, n-propanol, n-butanol, n-butylene glycol, glycerin, diethylene glycol monoethyl ether, and diethylene glycol mono-n-butyl ether. Preference here is given to all water-soluble organic solvents. In the context of the invention, an aqueous carrier comprises at least 30 wt. %, especially at least 50 wt. % water, based on total weight of the application mixture.

As a first feature, agents according to the invention comprise a non-ionic component having an HLB value of 8.0 or less. In the context of the invention, 'non-ionic' means that the component does not form ions in aqueous solution.

Without being bound by any theory, it is believed that hydrophobic interactions between the non-ionic component and the substantive dyes afford a protection to these dyes under the aggressive conditions of the blonding agent. HLB value is a measure introduced by Griffin (1950) for the water- or oil-solubility of compounds, wherein compounds with low HLB values exhibit more hydrophobic properties than compounds having high HLB values. For the definition of the HLB value, reference is expressly made to the explanations in Hugo Janistyn, Handbuch der Kosmetika und Riechstoffe, Vol. III: Die Körperpflegemittel, $2^{nd}$ Ed., Dr. Alfred Hüthig Verlag Heidelberg (1973), pp. 68-78 and Hugo Janistyn, Taschenbuch der modernen Parfümerie und Kosmetik, $4^{th}$ Ed., Wissenschaftliche Verlagsgesellschaft m. b. H. Stuttgart (1974), pp. 466-474, as well as the original works cited therein.

In the context of the invention, fats, oils, waxes or even non-ionic emulsifiers can be used as non-ionic components having an HLB value of 8.0 or less. In the context of the invention, fats and oils refer to generally solid, semi-solid or liquid, more or less viscous products of vegetal or animal bodies that substantially consist of mixed triglycerides of higher fatty acids.

Preferably useable vegetal oils are macadamia nut oil, candle nut oil, palm oil, amaranth seed oil, peach stone oil, avocado oil, olive oil, cocoa oil, rape seed oil, sesame oil, jojoba oil, soja oil, peanut oil, evening primrose oil and tea tree oil.

Mineral oils, especially paraffin oils or waxes, can be inventively used. Waxes can be likewise used, especially esters of long chain $C_{24}$-$C_{36}$ fatty acids (wax acids) with long chain alcohols (fatty alcohols), triterpene or steroid alcohols (e.g., ambreine, betuline), which are widely present in plants and animals. They include, for example, natural waxes from living sources such as beeswax or carnauba wax, which also comprise free carboxy and hydroxy groups that bring about the emulsification capability of the so-called soap waxes, and in addition, natural fossil waxes (e.g., from brown coal or oil) mainly consisting, similarly to waxes from the Fischer-Tropsch Synthesis or polyethylene waxes, as straight chain hydrocarbons; fossil waxes; however, depending on their origin, may also comprise branched or cycloaliphatic hydrocarbons.

In a preferred embodiment, the agent according to the invention has a non-ionic emulsifier having an HLB value of 8.0 or less. Non-ionic emulsifiers are understood to include surface-active substances that do not form any ions in aqueous solution. The carrier of the surface-active effect is therefore the whole molecule. The hydrophilicity of such non-ionic emulsifiers is obtained through the fraction of polar groups in the molecule. Non-ionic emulsifiers include fatty alcohols, polymerization products of ethylene oxide and propylene oxide on saturated or unsaturated fatty alcohols, fatty acid esters of polyhydric alcohols with saturated or unsaturated fatty acids, alkyl esters of saturated or unsaturated fatty acids or alkylphenols and their alkoxylates.

Preferred non-ionic components are fatty alcohols having 6 to 30 carbon atoms in their alkyl chain. In this regard, the alkyl chain can be one or more than one branch, as well as cis and/or trans double bonds. Examples are hexyl alcohol (caproyl alcohol), heptyl alcohol (enanthyl alcohol), octyl alcohol (capryl alcohol), nonyl alcohol (pelargonyl alcohol), undecyl alcohol, undec-10-en-1-ol, dodecyl alcohol (lauryl alcohol), 2,6,8-trimethyl-4-nonanol (isolauryl alcohol), tridecyl alcohol, tetradecyl alcohol (myristyl alcohol), pentadecyl alcohol, hexadecyl alcohol (cetyl alcohol, or palmityl alcohol), heptadecyl alcohol, octadecyl alcohol (stearyl alcohol), isostearyl alcohol, (9Z)-octadec-9-en-1-ol (oleyl alcohol), (9E)-Octadec-9-en-1-ol (elaidyl alcohol), (9Z,12Z)-octadeca-9,12-dien-1-ol (linoleyl alcohol), (9Z,12Z,15Z)-octadeca-9,12,15-trien-1-ol (linolenyl alcohol), nonadecan-1-ol (nonadecyl alcohol), eicosan-1-ol (eicosyl alcohol/arachyl alcohol), (9Z)-eicos-9-en-1-ol (gadoleyl alcohol), (5Z,8Z,11Z,14Z)-eicosa-5,8,11,14-tetraen-1-ol (arachidonyl alcohol), heneicosyl alcohol, docosyl alcohol (behenyl alcohol), (13Z)-docos-13-en-1-ol (erucyl alcohol) and (13E)-docosen-1-ol (brassidyl alcohol). According to the invention, it is possible to employ mixtures of fatty alcohols obtained by controlled mixing or by extraction processes. Examples are cocoa alcohol (mixture of $C_8$-$C_{18}$ fatty alcohols) and cetearyl alcohol (1:1-mixture of $C_{16}$ and $C_{18}$ fatty alcohols).

Further preferred non-ionic components having an HLB value of 8.0 or less are ethylene glycol ethers with fatty alcohols. In principle, ethylene glycol ethers of the abovementioned fatty alcohols can be used. In order to obtain an HLB value in the inventive range, it is preferred to use ethylene glycol ethers with fatty acids having the lowest possible ethoxylation degree. Here, ethoxylation degree refers to the molar quantity of ethylene oxide employed per mole of fatty alcohol. Ethylene glycol ethers with an ethoxylation degree of 1 (fatty alcohol monoethylene glycol ethers), 2 (fatty alcohol diethylene glycol ethers) or 3 (fatty alcohol triethylene glycol ethers) are preferred. Exemplary, inventively preferred ethylene glycol ethers are Laureth-1, Laureth-2, Laureth-3, Isolaureth-1, Isolaureth-2, Isolaureth-3, Trideceth-1, Trideceth-2, Trideceth-3, Myreth-1, Myreth-2, Myreth-3, Ceteth-1, Ceteth-2, Ceteth-3, Steareth-1, Steareth-2, Steareth-3, Oleth-1, Oleth-2, Oleth-3, Ceteareth-1, Ceteareth-2, Ceteareth-3, Coceth-1, Coceth-2, Cocoeth-3, Pareth-1, Pareth-2 and Pareth-3. Ceteth-1, Laureth-2, Ceteth-2, Steareth-2, Oleth-2, Laureth-3, Isolaureth-3, Trideceth-3, Ceteareth-3 and Oleth-3 are particularly preferred.

Further preferred non-ionic components having an HLB value of 8.0 or less are addition products of fatty alcohols with propylene oxide. In principle, propylene glycol ethers of the abovementioned fatty alcohols can be used, wherein propylene glycol ethers with fatty alcohols with a low propoxylation degree are preferred. Here, the propoxylation degree refers to the molar quantity of propylene oxide employed per mole of fatty alcohol. Propylene glycol ethers with a propoxylation degree of 1 to 3 are preferred. Exemplary, inventively preferred propylene glycol ethers are PPG-1 lauryl ether, PPG-2 lauryl ether, PPG-3 lauryl ether, PPG-1 isolauryl ether, PPG-2 isolauryl ether, PPG-3 isolauryl ether, PPG-1 tridecyl ether, PPG-2 tridecyl ether, PPG-3 tridecyl ether, PPG-2 myristyl ether, PPG-3 myristyl ether, PPG-1 cetyl ether, PPG-2 cetyl ether, PPG-3 cetyl ether, PPG-1 stearyl ether, PPG-2 stearyl ether, PPG-3 stearyl ether, PPG-1 oleyl ether, PPG-2 oleyl ether, PPG-3 oleyl ether, PPG-1 cetearyl ether, PPG-2 cetearyl ether, PPG-3 cetearyl ether, PPG-1 cocoyl ether, PPG-2 cocoyl ether and PPG-3 cocoyl ether. PPG-3 myristyl ether is particularly preferred.

It is also possible to use mixed ethylene and propylene glycol ethers with fatty alcohols as the non-ionic components having an HLB value of 8.0 or less.

According to the invention, likewise preferred employable non-ionic emulsifiers are fatty acid esters of polyhydric alcohols with saturated or unsaturated fatty acids with 8 to 22, especially 10 to 18, carbon atoms in the fatty acid group, provided that the criterion of an HLB value of 8.0 or less is fulfilled.

Here, ethylene glycol, propylene glycol, glycerin, pentaerythritol, sorbitan or sugar as well as their homo- or hetero-oligomers are preferred polyhydric alcohols.

Inventive esters of ethylene glycol or propylene glycol include mono-fatty acid esters as well as di-fatty acid esters with (poly)ethylene glycols and/or (poly)propylene glycols. Exemplary preferred fatty acids are lauric, myristic, palmitic, stearic, isostearic and oleic acids. Here, preferred compounds include ethylene glycol monofatty acid esters, propylene glycol monofatty acid esters, ethylene glycol difatty acid esters, polyethylene glycol monofatty acid esters and polyethylene glycol difatty acid esters. Exemplary, inventively particularly preferred compounds are ethylene glycol distearate, ethylene glycol monostearate, propylene glycol monostearate, diethylene glycol monostearate, polyethylene glycol (100) monostearate, polyethylene glycol (200) monostearate, diethylene glycol monolaurate, polyethylene glycol (200) dilaurate, polyethylene glycol (100) monolaurate, polyethylene glycol (100) monooleate, polyethylene glycol (200) dioleate or polyethylene glycol (400) dioleate.

Mono-, di- or trifatty acid esters on glycerin, its oligomers or its addition products with ethylene oxide and/or propylene oxide are likewise preferred. Glycerin monofatty acid esters, glycerin difatty acid esters and glycerin trifatty acid esters are particularly preferred. Exemplary compounds of this type are glyceryl trilaurate, glyceryl trimyristate, glyceryl tripalmitate, glyceryl tristearate, glyceryl triisostearate, glyceryl trioleate, glyceryl tricocoate, glyceryl dilaurate, glyceryl dimyristate, glyceryl dipalmitate, glyceryl distearate, glyceryl diisostearate, glyceryl dioleate, glyceryl dicocoate, glyceryl monolaurate, glyceryl monomyristate, glyceryl monopalmitate, glyceryl monostearate, glyceryl monoisostearate, glyceryl monooleate and glyceryl monococoate. Mono- or polyfatty acid esters on polyglycerides are also additional employable non-ionic components. Examples of these are decaglycerin decaoleate, decaglycerin octaoleate, decaglycerin decastearate, triglyceryl diisostearate or diglycerin monostearate.

It is likewise possible to employ triglycerides of fatty acids that carry hydroxyl groups, especially castor oil, which can be used in hydrogenated or non-hydrogenated form. Ethoxylated castor oil is particularly preferred.

Likewise preferred, inventive non-ionic components are fatty acid esters of pentaerythritol, especially pentaerythritol monofatty acid esters. Examples of these compounds are pentaerythritol monolaurate, pentaerythritol monomyristate, pentaerythritol monopalmitate, pentaerythritol monostearate and pentaerythritol monooleate.

Equally preferred, inventive non-ionic components are fatty acid esters of sorbitan as the polyhydric alcohol, especially sorbitan monofatty acid esters, sorbitan difatty acid esters and sorbitan trifatty acid esters. Examples of these compounds are sorbitan trioleate, sorbitan tristearate, sorbitan tripalmitate, sorbitan trimyristate, sorbitan triisostearate, sorbitan trilaurate, sorbitan dioleate, sorbitan distearate, sorbitan dipalmitate, sorbitan dimyristate, sorbitan disostearate, sorbitan dilaurate, sorbitan monooleate, sorbitan monostearate, sorbitan monopalmitate, sorbitan monomyristate, sorbitan monoisostearate and sorbitan monolaurate.

Fatty acid di- or polyesters with sugars, especially with saccharose, optionally as their addition products with propylene oxide and/or ethylene oxide, are also inventively preferably employed, provided that these compounds possess an HLB value of 8.0 or less. Examples of such compounds are inter alfa saccharose dilaurate, saccharose dimyristate, saccharose dipalmitate, saccharose distearate, saccharose dioleate, saccharose tristearate and polypropylene glycol saccharose tetrapalmitate.

Esters of non-hydroxylated $C_6$-$C_{30}$ alkyl monocarboxylic acids with optionally branched, $C_1$-$C_{30}$ monoalcohols are preferably inventively suitable as the alkyl esters of saturated or unsaturated fatty acids. The monoesters of fatty acids with monoalcohols having 2 to 24 carbon atoms are preferred. Examples of fatty acid moieties utilized in the esters are caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachidonic acid, gadoleic acid, behenic acid and erucic acid as well as their industrial mixtures that, for example, result from cracking natural fats and oils, from the oxidation of aldehydes from Roelen's Oxo Synthesis or from the dimerization of unsaturated fatty acids. Examples of fatty alcohol moieties in the esters are isopropyl alcohol, caproyl alcohol, capryl alcohol, 2-ethylhexyl alcohol, 1-decanol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol and brassidyl alcohol as well as their industrial mixtures that, for example, result from the high pressure hydrogenation of industrial methyl esters based on fats and oils or aldehydes from Roelen's Oxo Synthesis as well as the monomer fraction on the dimerization of unsaturated fatty alcohols. Isopropyl myristate, cetearyl isononanoate, 2-ethylhexyl palmitate, 2-ethylhexyl stearate, cetyl oleate, cocoyl caprinate/caprylate, n-butyl stearate, oleyl erucate, isopropyl palmitate, oleyl oleate, hexyl laurate, myristyl myristate, cetearyl isononanoate or decyl oleate are inventively particularly preferred.

Finally, alkoxylated fatty acid esters of the Formula RC(O)—(OCH$_2$CH$_2$)$_w$OR', wherein RC(O)— is a linear or branched, saturated and/or unsaturated acyl group with 6 to 22 carbon atoms, R' is linear or branched alkyl groups with 1 to 4 carbon atoms, and w is a number from 1 to 20, can also be employed as the non-ionic components, provided that they have an HLB value of 8.0 or less.

Alkylphenols and their addition products on ethylene oxide and/or propylene oxide having an HLB value of 8.0 or less also represent a further inventively preferred class of non-ionic components. In this regard, preferred compounds have 6 to 21, especially 6 to 15 carbon atoms in the alkyl chain. Preferred representatives of these compounds are octylphenol and nonylphenol, optionally alkoxylated with 1 to 3 moles ethylene oxide and/or propylene oxide. Octoxynol-1, Octoxynol-2, Octoxynol-3, Nonoxynol-1, Nonoxynol-2 and Nonoxynol-3 may be listed as particularly preferred examples.

Accordingly, a preferred embodiment of the present invention includes non-ionic components with an HLB value of 8.0 or less chosen from fatty alcohols, fatty alcohol monoethylene glycol ethers, fatty alcohol diethylene glycol ethers, fatty alcohol triethylene glycol ethers, glycerin monofatty acid esters, glycerin difatty acid esters, glycerin trifatty acid esters, sorbitan monofatty acid esters, sorbitan difatty acid esters, sorbitan trifatty acid esters, pentaerythritol monofatty acid esters, ethylene glycol monofatty acid esters, ethylene glycol difatty acid esters, polyethylene glycol monofatty acid esters, polyethylene glycol difatty acid esters, saccharose monofatty acid esters, saccharose difatty acid esters, propylene glycol monofatty acid esters and fatty acid alkyl esters.

Inventively particularly preferred agents have at least one fatty alcohol as the non-ionic component having an HLB value of 8.0 or less. Fatty alcohols containing 12, 14, 16 or 18 carbon atoms in the alkyl chain are particularly preferred.

In this regard, the agent preferably includes one or more non-ionic components with an HLB value of 8.0 or less in an amount of 1.0 wt. % to 50 wt. %, particularly 2.0 wt. % to 25 wt. % and quite particularly preferably 3.0 wt. % to 15 wt. %, based on total weight of the ready for use agent.

Agents according to the invention also include a combination of at least one blue substantive dye and one red substantive dye, wherein the value of the weight ratio between the sum of all blue substantive dyes and the sum of all red substantive dyes is greater than or equal to 1.

This enables unwanted color shifts towards rosy/pink colored nuances to be avoided.

Inventively preferred agents are those wherein the total weight of all blue substantive dyes is greater than the total weight of all red substantive dyes.

Accordingly, preferred agents are those wherein the value of the weight ratio between the sum of all blue substantive dyes and the sum of all red substantive dyes is from 1 to 100, preferably from 1.5 to 10 and particularly preferably from 2 to 4.

wherein R1, R2, R3, R4, R5, R6, R7 and R8 are each, independently, hydrogen, fluorine, chlorine, bromine, iodine, a hydroxyl group or a nitro group.

Depending on the pH of the agent, the compound according to Formula (I) is present in deprotonated form as one of its physiologically acceptable salts. Here, physiologically acceptable salts are salts of alkali metals, alkaline earth metals or ammonium, wherein ammonium itself as well as primary, secondary, tertiary or quaternary substituted ammonium salts can be employed. These include the salts of the cations 2-hydroxyethylammonium, di(2-hydroxyethyl)ammonium, tri(2-hydroxyethyl)ammonium, triethylammonium and tetraethylammonium. Preferred salts of the compound according to Formula (I) are sodium, potassium, magnesium, calcium and ammonium salts.

Furthermore, depending on the pH, compounds according to Formula (I) exist in tautomeric equilibrium with their cyclized form according to Formula (Ia) and/or with one of their physiologically acceptable salts.

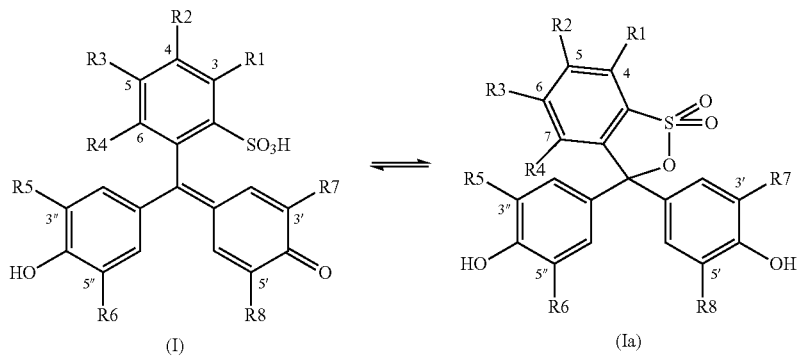

(I)                                    (Ia)

Both structural Formulas (I) and (Ia) therefore inventively reflect the same compound.

Preferred agents include a compound according to Formula (I) and/or one of its physiologically acceptable salts as the blue substantive dye, wherein at least one of the substituents R1, R2, R3 and/or R4 is fluorine, chlorine, bromine or iodine. Particularly preferred agents include at least one compound according to Formula (I) as the blue substantive dye chosen from compounds according to Formula (I) and/or one of their physiologically acceptable salts, wherein— a) R1, R2, R3, R4, R5, R6, R7 and R8 are bromine;
b) R1, R4, R5, R6, R7 and R8 are bromine and R2 and R3 are hydrogen;
c) R1 and R4 are hydrogen and R2, R3, R5, R6, R7 and R8 are bromine;
d) R1, R2, R3 and R4 are fluorine and R5, R6, R7 and R8 are bromine;
e) R1, R2, R3 and R4 are chlorine and R5, R6, R7 and R8 are bromine;
f) R1, R2, R3 and R4 are iodine and R5, R6, R7 and R8 are bromine;
g) R1, R2, R3, R4, R5, R6, R7 and R8 are chlorine;
h) R1, R2, R3 and R4 are bromine and R5, R6, R7 and R8 are chlorine;
i) R1 and R4 are bromine, R2 and R3 are hydrogen and R5, R6, R7 and R8 are chlorine;
j) R1 and R4 are hydrogen, R2 and R3 are bromine and R5, R6, R7 and R8 are chlorine;

In principle, there are no limits imposed on choice of the substantive dyes. Inventively employable substantive dyes include nitrophenylenediamines, nitroamino phenols, azo dyes, anthraquinones or indophenols. Substantive dyes are usually classified as anionic, cationic and non-ionic substantive dyes.

However, it is particularly inventively advantageous when the substantive dyes possess satisfactory stability towards the harsh conditions of the blonding process.

The agent preferably includes at least one anionic substantive dye as the blue substantive dye. In a preferred embodiment, the agent has at least one compound according to Formula (I) below and/or one of its physiologically acceptable salts as the blue substantive dye.

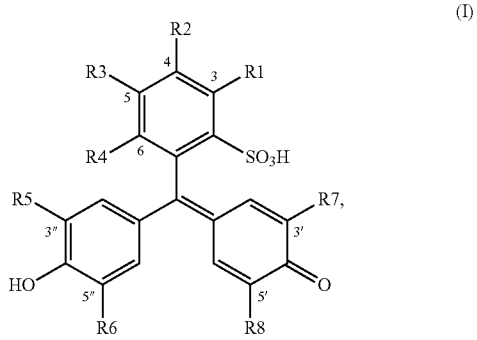

(I)

k) R1, R2, R3 and R4 are iodine and R5, R6, R7 and R8 are chlorine;
l) R1, R2, R3, R4, R5, R6, R7 and R8 are iodine;
m) R1, R2, R3 and R4 are fluorine and R5, R6, R7 and R8 are iodine;
n) R1, R2, R3 and R4 are chlorine and R5, R6, R7 and R8 are iodine; or ethylammonium. Preferred salts of the compound according to Formula (I) are sodium, potassium, magnesium, calcium and ammonium salts.

Furthermore, depending on the pH, compounds according to Formula (II) exist in a tautomeric equilibrium with their cyclized form according to Formula (IIa) and/or with one of their physiologically acceptable salts.

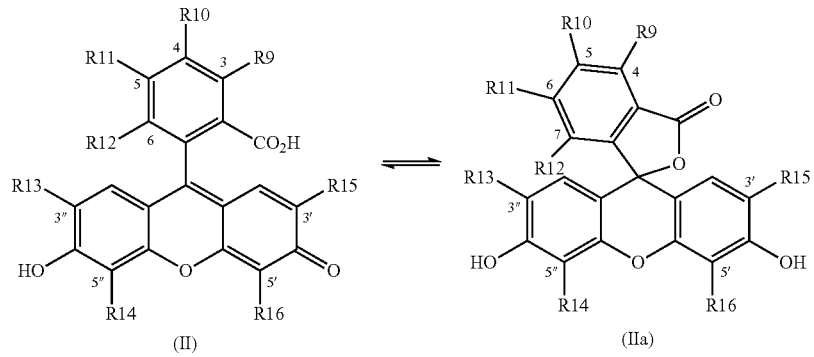

(II)          (IIa)

o) R1, R2, R3 and R4 are bromine and R5, R6, R7 and R8 are iodine.

Quite preferably the agent includes a compound according to Formula (I) and/or one of its physiologically acceptable salts, wherein the groups R1, R2, R3, R4, R5, R6, R7 and R8 are bromine. This compound is also known as tetrabromophenol blue.

The agent preferably includes at least one anionic substantive dye as the red substantive dye, preferably from the group of fluorescein dyes.

In a preferred embodiment, the agent has at least one compound according to Formula (II) below and/or one of its physiologically acceptable salts as the red substantive dye.

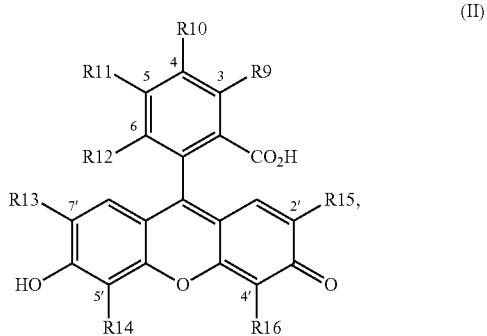

(II)

Wherein R9, R10, R11, R12, R13, R14, R15 and R16 are each, independently, hydrogen, fluorine, chlorine, bromine, iodine, a hydroxyl group or a nitro group.

Depending on the pH of the agent, the compound according to Formula (II) is present in deprotonated form as one of its physiologically acceptable salts. Here, physiologically acceptable salts are salts of alkali metals, alkaline earth metals or ammonium, wherein ammonium itself as well as primary, secondary, tertiary or quaternary substituted ammonium salts can be employed. They include salts of the cations 2-hydroxyethylammonium, di(2-hydroxyethyl)ammonium, tri(2-hydroxyethyl)ammonium, triethylammonium and tetra- Both structural Formulas (II) and (IIa) therefore inventively reflect the same compound.

Preferred agents include a compound according to Formula (I) and/or one of its physiologically acceptable salts as the blue substantive dye, wherein at least one of the substituents R9, R10, R11 and/or R12 is hydrogen, chlorine, bromine or iodine.

Particularly preferred agents include at least one compound as the blue substantive dye chosen from compounds according to Formula (I) and/or one of their physiologically acceptable salts, wherein
a) R9, R10, R11 and R12 are chlorine and R13, R14, R15 and R16 are bromine (known as Acid Red 92);
b) R9 and R12 are chlorine, R11 and R12 are for hydrogen and R13, R14, R15 and R16 are bromine (known as Acid Red 98);
c) R9, R10, R11 and R12 are chlorine and R13, R14, R15 and R16 are iodine (known as Acid Red 94);
d) R9, R10, R11 and R12 are hydrogen and R13, R14, R15 and R16 are bromine (known as Acid Red 87); or
e) R9, R10, R11 and R12 are hydrogen and R13, R14, R15 and R16 are iodine (known as Acid Red 51).

The agent quite preferably includes a compound according to Formula (II) and/or one of its physiologically acceptable salts, wherein R9, R10, R11 and R12 are chlorine and R13, R14, R15 and R16 are bromine (known as Acid Red 92). This compound is also known as D&C RED No. 28 or Phloxin B.

Inventively preferred dye combinations are those with at least the combination of tetrabromophenol blue and Acid Red 92; tetrabromophenol blue and Acid Red 98; tetrabromophenol blue and Acid Red 94; tetrabromophenol blue and Acid Red 87 or tetrabromophenol blue and Acid Red 51.

The agent quite particularly preferably includes at least one combination of a compound according to Formula (I), wherein R1, R2, R3, R4, R5, R6, R7 and R8 are bromine, and a compound according to Formula (II), wherein R9, R10, R11 and R12 are chlorine and R13, R14, R15 and R16 are bromine (tetrabromophenol blue and Acid Red 92).

It can also be inventively preferred for the agent to have further substantive dyes. Preferably, the agent includes a yellow and/or orange dye as the further substantive dye.

This is particularly advantageous when unwanted reddish color shifts appear in the blonding process.

Yellow dyes are preferably chosen from suitable yellow nitro dyes such as 1,2-diamino-4-nitrobenzene (cl. 76,020), 1-[(2-hydroxyethypamino]-2-nitrobenzene (HC yellow 2), 1-(2-hydroxyethoxy)-2-[(2-hydroxyethypamino]-5-nitrobenzene (HC yellow 4), 1-amino-2-[(2-hydroxyethyl)amino]-5-nitrobenzene (HC yellow 5), 4-[(2,3-dihydroxypropyl)amino]-3-nitro-1-trifluoromethylbenzene (HC yellow 6), 2-[di(2-hydroxyethypamino]-5-nitrophenol, 2-[(2-hydroxyethyl)amino]-1-methoxy-5-nitrobenzene, 2-amino-3-nitrophenol, 2-amino-4-nitrophenol, 1-amino-2-methyl-6-nitrobenzene, 1-(2-hydroxyethoxy)-3-methylamino-4-nitrobenzene, 2,3-(dihydroxypropoxy)-3-methylamino-4-nitrobenzene, 3-[(2-aminoethyl)amino]-1-methoxy-4-nitrobenzene hydrochloride (HC yellow 9), 1-chloro-2,4-bis[(2-hydroxyethyl)amino]-5-nitrobenzene (HC yellow 10), 2-[(2-hydroxyethyl)amino]-5-nitrophenol (HC yellow 11), 1-[(2'-ureidoethyl)amino]-4-nitrobenzene, 1-amino-4-[(2-aminoethyl)-amino]-5-methyl-2-nitrobenzene, 4-[(2-hydroxyethyl)amino]-3-nitro-1-methylbenzene, 1-chloro-4-[(2-hydroxyethyl)amino]-3-nitrobenzene (HC yellow 12), 4-[(2-hydroxyethypamino]-3-nitro-1-trifluoromethylbenzene (HC yellow 13), 4-[(2-hydroxyethyl)-amino]-3-nitro-benzonitrile (HC yellow 14), 4-[(2-hydroxyethyl)amino]-3-nitro-benzamide (HC yellow 15), 3-[(2-hydroxyethyl)amino]-4-methyl-1-nitrobenzene, 4-chloro-3-[(2-hydroxyethyl)amino]-1-nitrobenzene.

Suitable yellow or orange quinone dyes include 2-[(2-aminoethyl)amino]-9,10-anthraquinone (HC Orange 5) and 2-hydroxy-1,4-naphthaquinone (Cl. 75,480, Natural Orange 6). Neutral, yellow or orange azo dyes can also be inventively advantageously employed, especially 4-[(4-aminophenyl)azo]-1-[di(2-hydroxyethyl)amino]-3-methylbenzene (HC Yellow 7), 2,6-diamino-3-[(pyridin-3-yl)azo]pyridine, 2-{[4-(acetylamino)phenyl]azo}-4-methylphenol (Cl. 11855; Disperse Yellow 3), 4-[(4-nitrophenyl)azo]aniline (Cl. 11,005; Disperse Orange 3).

Suitable yellow or orange, anionic substantive dyes include 6-hydroxy5-[(4-sulfophenyl)azo]-2-naphthalene sulfonic acid disodium salt (Cl. 15,985; Food Yellow No. 3; FD&C Yellow No. 6), 2,4-dinitro-1-naphthol-7-sulfonic acid disodium salt (Cl. 10,316; Acid Yellow 1; Food Yellow No. 1), 2-(indane-1,3-dion-2-yl)quinoline-x,x-sulfonic acid (mixture of mono- and disulfonic acids) (Cl. 47,005; D&C Yellow No. 10; Food Yellow No. 13; Acid Yellow 3, Yellow 10), 4-((4-amino-3-sulfophenyl)azo)benzene sulfonic acid disodium salt (Cl. 13,015, Acid Yellow 9), 5-hydroxy-1-(4-sulfophenyl)-4-[(4-sulfophenyl)azo]pyrazol-3-carboxylic acid trisodium salt (Cl. 19,140; Food Yellow No. 4; Acid Yellow 23), 3-[(4-phenylamino)phenyl]azobenzene sulfonic acid sodium salt (Cl. 13,065; Ki406; Acid Yellow 36), 9-(2-carboxyphenyl)-6-hydroxy-3H-xanthen-3-one (Cl. 45,350; Acid Yellow 73; D&C Yellow No. 8), 5-[(2,4-dinitrophenyl)amino]-2-phenylaminobenzene sulfonic acid sodium salt (Cl. 10,385; Acid Orange 3), 4-[(2,4-dihydroxyphenyl)azo]benzene sulfonic acid sodium salt (Cl. 14,270; Acid Orange 6), 4-[(2-hydroxynaphth-1-yl)azo]benzene sulfonic acid sodium salt (Cl. 15,510; Acid Orange 7), 4-[(2,4-dihydroxy-3-[(2,4-dimethylphenyl)azo]phenyl)azo]benzene sulfonic acid sodium salt (Cl. 20,170; Acid Orange 24).

Suitable cationic substantive dyes include 3-[(4-amino-2,5-dimethoxyphenyl)azo]-N,N,N-trimethylbenzeneaminium chloride (Cl. 12,605, Basic Orange 69), di[4-(dimethylamino)phenyl]iminomethane hydrochloride (Cl. 41,000; Basic Yellow 2), 2-[2-((2,4-dimethoxyphenyl)amino)ethenyl]-1,3,3-trimethyl-3H-indol-1-ium chloride (Cl. 48,055; Basic Yellow 11), 3-methyl-1-phenyl-4-[(3-(trimethylammonio)phenyl)azo]-pyrazol-5-one chloride (Cl. 12,719; Basic Yellow 57). Preferred yellow or orange, cationic substantive dyes are Basic Yellow 87 and Basic Orange 31.

Particularly preferred yellow or orange, non-ionic substantive dyes are those known under the international designations or trade names HC Yellow 2, HC Yellow 4, HC Yellow 5, HC Yellow 6, HC Yellow 12, HC Yellow 13, HC Orange 1 and Disperse Orange 3, especially HC Yellow 13.

A second subject matter of the present application is method of manufacturing an agent for bleaching keratinic fibers by blending at least one oxidizing agent preparation (B) having at least one oxidizing agent chosen from hydrogen peroxide and its addition products on solid carriers, and at least one preparation (A), wherein preparation (A) has in a cosmetic carrier at least one non-ionic component having an HLB value of 8.0 or less and a combination of at least one blue substantive dye and one red substantive dye, wherein the value of the weight ratio between the sum of all blue substantive dyes and the sum of all red substantive dyes is greater than or equal to 1.

According to the invention, in order to obviate potential instabilities, it has proven to be particularly favorable to provide the bleaching agent initially separated into oxidizing agent preparation (B) and preparation (A) comprising the dyes responsible for the matting effect.

Inventive agents for blonding keratinic fibers include at least one oxidizing agent preparation (B). This preparation has at least one oxidizing agent chosen from hydrogen peroxide and its addition compounds on solid carriers.

Hydrogen peroxide is preferably used as the oxidizing agent according to the invention. Hydrogen peroxide is added as a solution or in the form of a solid addition compound of hydrogen peroxide onto inorganic or organic compounds such as sodium perborate, sodium percarbonate, magnesium percarbonate, sodium percarbamide, polyvinyl pyrrolidone.n $H_2O_2$ (n is a positive integer greater than 0), urea peroxide and melamine peroxide.

Aqueous hydrogen peroxide solutions are particularly preferred. The concentration of a hydrogen peroxide solution is firstly determined from the statutory regulations and secondly according to the required effect. Generally, 3 to 12 percent solutions in water are used.

Agents according to the invention preferably include hydrogen peroxide. Here, inventive agents for blonding keratinic fibers are particularly preferred which comprise 0.5 to 18 wt. %, preferably 1 to 15 wt. %, particularly preferably 2.5 to 12 wt. % and especially 3 to 9 wt. % hydrogen peroxide (calculated as 100% concentrated $H_2O_2$).

Oxidizing agent preparations (A) according to the invention are preferably aqueous, free-flowing oxidizing agent preparations. In this regard, preferred preparations are those wherein the free-flowing oxidizing agent preparation—based on its weight—comprises 40 to 98 wt. %, preferably 60 to 97.5 wt. %, particularly preferably 70 to 97 wt. % more preferably 75 to 96 wt. % and particularly 80 to 95 wt. % water.

According to the invention, the oxidizing agent preparation can also be applied to hair together with a catalyst that activates oxidation of the dye precursors (e.g., by atmospheric oxygen). Such catalysts include certain enzymes, iodides, quinones or metal ions. Suitable enzymes are, for example, peroxidases, which can considerably enhance the effect of small amounts of hydrogen peroxide. An addition of certain metal ions or metal complexes can likewise be preferred. Suitable metal ions are for example $Zn^{2+}$, $Cu^{2+}$, $Fe^{2+}$, $Fe^{3+}$, $Mn^{2+}$, $Mn^{4+}$, $Li^{+}$, $Mg^{2+}$, $Ca^{2+}$, $Ce^{4+}$, $V^{3+}$, $Co^{2+}$, $Ru^{3+}$ and $Al^{3+}$.

The ready for use blonding agent of preparation (A) and oxidizing agent preparation (B) preferably has a pH in the range 6 to 12. The application is more preferably in alkaline medium. Application temperatures can be in a range from 15 to 40° C. After a contact time of 2 to 60, preferably 5 to 45 minutes, the blonding agent is rinsed out of the hair. There is no need to subsequently wash the hair with a shampoo if a strong surfactant-containing carrier is used.

In addition, it has proven advantageous for the oxidizing agent preparations to have at least one stabilizer or complexant. Particularly preferred stabilizers are phenacetin, alkali benzoates (sodium benzoate) and salicylic acid. The addition of complexants is also inventively preferred. Complexants are substances that can complex metal ions. Preferred complexants are chelating complexants. Inventively preferred complexants are nitrogen-containing polycarboxylic acids, especially EDTA, and phosphonates, preferably hydroxyalkane or aminoalkane phosphonates and especially 1,1-hydroxyethane-1,1-diphosphonate (HEDP) or its di- or tetrasodium salt and/or ethylenediaminetetramethylene phosphonate (EDTMP) or its hexasodium salt and/or diethylenetriaminepentamethylene phosphonate (DTPMP) or its hepta- or octasodium salt.

Oxidizing agent preparation (B) can have additional auxiliaries and additives in addition to the actual oxidizing agent and optional complexant. Thus, it has proven to be inventively preferred when the oxidizing agent preparation has at least one thickener. There are no limitations with respect to choice of thickener. Both organic as well as purely inorganic thickeners can be used.

According to a first preferred embodiment, the thickener is an anionic, synthetic polymer. Preferred anionic homopolymers are commercially available under the trade name Carbopol®, for example. The homopolymer of 2-acrylamido-2-methylpropane sulfonic acid, commercially available, for example, under the trade name Rheothik® 11-80, is likewise preferred. Preferred anionic copolymers include copolymers of acrylic acid, methacrylic acid or their $C_1$-$C_6$ alkyl esters, as are commercialized under the INCI name Acrylates Copolymers. A preferred commercial product is, for example, Aculyn® 33 from Rohm & Haas. Further preferred copolymers are commercialized by Rohm & Haas under the trade name Aculyn® 22, as well as by National Starch under the trade names Structure@ 2001 and Structure® 3001 and Carbopol® ETD 2020, Carbopol® Ultrez 20 and Pemulen TR-1 from Lubrizol. Additionally preferred anionic copolymers are acrylic acid-acrylamide copolymers, as comprised in the commercial products Sepigel® 305 and Simulgel® 600 from SEPPIC. Additionally preferred anionic copolymers are sold under the trade names Aristoflex® AVC or Aristoflex® HMB by Clariant. Polymers of maleic anhydride and methyl vinyl ether, such as the commercially available copolymer Stabilize® QM, are preferred thickeners. The inventive agent can preferably additionally comprise at least one anionic polymer or copolymer of acrylic acid and/or methacrylic acid, such as Latekoll® D (BASF).

According to a second embodiment, the thickener is a cationic, synthetic polymer. A particularly suitable homopolymer is poly(methacryloyloxyethyltrimethylammonium chloride) with the INCI name Polyquaternium-37. Its polymer dispersions are commercially available under the trade names Salcare® SC 92, Salcare® SC 95 and Salcare® SC 96.

In a third preferred embodiment, naturally occurring thickeners are employed. Non-modified guar gums are sold, for example, under the trade name Jaguar® C (Rhone Poulenc). Modified guar gums are commercially available under the trade names Jaguar® HP8, Jaguar® HP60, Jaguar® HP120, Jaguar® DC293 and Jaguar® HP105 (Rhone Poulenc). According to this embodiment, biosaccharide gums of microbial origin are further preferred, such as the scleroglucan gums or Xanthan gums, gums from vegetal exudates, such as gum arabicum, ghatti-gum, karaya gum, traganthe gum, carrageen gum, agar-agar, locust bean flour, pectins, alginates, starch fractions and derivatives such as amylose, amylopectin and dextrins, cellulose derivatives, such as for example methyl cellulose, carboxyalkyl celluloses and hydroxyalkyl celluloses (Cellosize®; Amerchol; Natrosol®; Hercules and Blanose®; Aqualon, Aquasorb®, Ambergum®; Hercules; Cellgon®; Montello). In addition, starches and their derivatives are preferred, for example, extracted from potatoes, manioc, yams, arrowroot, corn, cereals, rice, leguminous plants, bananas or the pith of certain types of palm (e.g. Amaze®; National Starch).

Non-ionic, fully synthetic polymers, such as polyvinyl alcohol or polyvinyl pyrrolidinone, can also be employed as the thickeners (Luviskol®; BASF). In the context of the invention, layered silicates have proven to be particularly suitable as the inorganic thickeners (Optigel®; Süd Chemie).

Inventively preferred agents for blonding keratinic fibers exhibit an alkaline pH. Another preferred embodiment of the present invention is where the ready for use agent has a pH from 7.0 to 12.0, preferably from 8.0 to 11.0. In the context of the present invention, pH values refer to those measured at a temperature of 22° C. The pH is usually adjusted with pH adjustors. The person skilled in cosmetics commonly uses established acidifiers and alkalizers to adjust the pH. The alkalizers that can be used for adjusting the pH are typically selected from inorganic salts, especially from the alkali and alkaline earth metals, organic alkalizers, especially amines, basic amino acids and alkanolamines, and ammonia. Inventively preferred acidifiers are food acids, such as for example citric acids, acetic acid, malic acid or tartaric acid, as well as diluted mineral acids. An especially preferred alkanolamine is monoethanolamine. Preparations according to the invention preferably include alkalizers in amounts of 0.2 to 25 wt. %, particularly 0.5 to 10 wt. %.

A particularly preferred presentation form of the agent is a kit-of-parts having at least one oxidizing agent preparation (B) and at least one preparation (A) in containers separate from each other, wherein preparation (A) has in a cosmetic carrier at least one non-ionic emulsifier having an HLB value of 8.0 or less and a combination of at least one blue substantive dye and one red substantive dye, wherein the value of the weight ratio between the sum of all blue substantive dyes and the sum of all red substantive dyes is 1 or greater.

Moreover, it can be particularly advantageous when the kit-of-parts has at least one additional hair treatment agent, especially a conditioner, in a separate container.

Furthermore, the packaging unit can include application aids such as combs, brushes or small brushes, personal protective clothing, especially disposable gloves, as well as an optional instruction manual. The above executions for the first and second subject matters of the invention are valid in regard to the preferred embodiments for the preparation (A) and the oxidizing agent preparation (B).

If a strong lightening is desired, then it is preferred to additionally mix a blonding preparation (C) having at least one bleach booster with the mixture of the oxidizing agent preparation (B) and preparation (A). In this regard, it is irrelevant whether a mixture (A) and (B) is initially produced and then the blonding preparation (C) is blended in, or whether a different sequence of blending of the individual components is utilized. It is preferred to blend the individual preparations in the shortest possible period of time and to apply the ready for use agent preferably promptly onto the keratinic fibers.

Consequently, another embodiment of the present application is a method of manufacturing an agent for bleaching keratinic fibers by blending at least one oxidizing agent preparation (B) having at least one oxidizing agent chosen from hydrogen peroxide and its addition products on solid carriers, at least one preparation (C) having at least one bleach booster, and at least one preparation (A), wherein preparation (A) has in a cosmetic carrier at least one non-ionic emulsifier having an HLB value of 8.0 or less and a combination of at least one blue substantive dye and at least one red substantive dye, wherein the value of the weight ratio between the sum of all blue substantive dyes and the sum of all red substantive dyes is greater than or equal to 1.

It is inventively particularly advantageous when the ready for use agent for bleaching keratinic fibers contains a total amount of substantive dyes in a range from 0.0001 to 0.2 wt. %, based on total weight of the ready for use agent.

Employing only hydrogen peroxide or its addition products on organic or inorganic compounds is often insufficient to strongly lighten very dark hair. Here, a combination of hydrogen peroxide and at least one bleach booster is generally employed, resulting in an agent having an increased lightening power.

In the context of the present invention, peroxy compounds, additional compounds that yield aliphatic peroxycarboxylic acids and/or substituted perbenzoic acids under perhydrolysis conditions, carbonic acid derivatives, alkyl carbonates, alkyl carbamates, silyl carbonates, silyl carbamates and nitrogen-containing, optionally cationic heterocycles, especially acylpyridinium and dihydroisoquinolinium salts, can be employed as the bleach booster.

The bleach booster is preferably chosen from ammonium persulfate, alkali metal persulfates, ammonium peroxymonosulfate, alkali metal hydrogen peroxymonosulfates, alkali metal peroxydiphosphates and alkaline earth metal peroxides. Particularly preferred bleach boosters are ammonium peroxydisulfate, potassium peroxydisulfate, sodium peroxydisulfate, potassium hydrogen peroxymonosulfate, potassium peroxydiphosphate, magnesium peroxide and barium peroxide. Inventively particularly preferred agents comprise at least one inorganic salt, selected from persulfates and/or peroxydisulfates, as the bleach booster in the blonding preparation (C). Moreover, the results of the work for the present invention have proven that the agents according to the invention should preferably comprise at least two different peroxydisulfates. In this regard, preferred peroxydisulfate salts are combinations of ammonium peroxydisulfate and potassium peroxydisulfate and/or sodium peroxydisulfate. The ready for use agent preferably includes peroxy compounds in an amount of 0.1 to 25 wt. %, particularly in an amount of 0.5 to 15 wt. %, based on total weight of the ready for use agent.

Persulfate salts or peroxydisulfate salts are generally added in the form of an optionally dedusted powder, paste or in the form of a compressed molded body.

Anhydrous preparations according to the invention include an additional bleach booster instead of or in addition to the solid peroxy compounds. Bleach activators that can be used are compounds which, under perhydrolysis conditions, yield aliphatic peroxycarboxylic acids having preferably 1 to 10 carbon atoms, particularly 2 to 4 carbon atoms, and/or optionally substituted perbenzoic acid. Substances which carry O-acyl and/or N-acyl groups of said number of carbon atoms and/or optionally substituted benzoyl groups are suitable. Preference is given to polyacylated alkylenediamines, particularly tetraacetyl ethylenediamine (TAED), acylated triazine derivatives, particularly 1,5-diacetyl-2,4-dioxohexahydro-1,3,5-triazine (DADHT), acylated glycolurils, particularly tetraacetyl glycoluril (TAGU), N-acylimides, in particular N-nonanoyl succinimide (NOSI), acylated phenol sulfonates, particularly n-nonanoyl- or isononanoyloxybenzene sulfonate (n- or iso-NOBS), carboxylic acid anhydrides, particularly phthalic anhydride, acylated polyhydric alcohols, particularly triacetin, ethylene glycol diacetate and 2,5-diacetoxy-2,5-dihydrofuran. Carbonate salts or hydrogen carbonate salts can be employed as the bleach boosters of the carbonic acid derivative type. They are preferably chosen from carbonate salts or hydrogen carbonate salts of ammonium, alkali metals (especially sodium and potassium) as well as of alkaline earth metals (especially magnesium and calcium). Particularly preferred carbonate or hydrogen carbonate salts are ammonium hydrogen carbonate, ammonium carbonate, sodium hydrogen carbonate, sodium carbonate, potassium hydrogen carbonate, potassium carbonate, magnesium carbonate and calcium carbonate. These preferred salts can be used as bleach boosters singly or in mixtures of at least two representatives. Furthermore, inventively employable bleach boosters can be nitrogen-containing, optionally cationic heterocycles. Imidazole may be mentioned as a particular example of a nitrogen-containing heterocyclic bleach booster.

Quaternized cations of pyridines and 3,4-dihydroisoquinolines are particularly preferred nitrogen-containing, heterocyclic bleach boosters. Here, preferred compounds are 4-acetyl-1-methylpyridinium p-toluene sulfonate, 4-acetyl-1-methylpyridinium benzene sulfonate, 4-acetyl-1-methylpyridinium bromide, 4-acetyl-1-methylpyridinium hydrogen sulfate, 4-acetyl-1-allylpyridinium p-toluene sulfonate, 4-acetyl-1-allylpyridinium benzene sulfonate, 4-acetyl-1-allylpyridinium bromide, 4-acetyl-1-allylpyridinium hydrogen sulfate, 4-acetyl-1-(2-hydroxyethyl)pyridinium p-toluene sulfonate, 4-acetyl-1-(2-hydroxyethyl)pyridinium benzene sulfonate, 4-acetyl-1-(2-hydroxyethyl)pyridinium bromide, 4-acetyl-1-(2-hydroxyethyl)pyridinium hydrogen sulfate, 4-acetyl-1-(2-oxopropyl)pyridinium p-toluene sulfonate, 4-acetyl-1-(2-oxopropyl)pyridinium benzene sulfonate, 4-acetyl-1-(2-oxopropyl)pyridinium bromide, 4-acetyl-1-(2-oxopropyl)pyridinium hydrogen sulfate, 4-acetyl-1-ethylpyridinium p-toluene sulfonate, 4-acetyl-1-ethylpyridinium benzene sulfonate, 4-acetyl-1-ethylpyridinium bromide, 4-acetyl-1-ethylpyridinium hydrogen sulfate, 4-acetyl-1-(2-methyl-prop-2-enyl)pyridinium p-toluene sulfonate, 4-acetyl-1-(2-methyl-prop-2-enyl)pyridinium benzene sulfonate, 4-acetyl-1-(2-methyl-prop-2-enyl)pyridinium bromide, 4-acetyl-1-(2-methyl-prop-2-enyl)pyridinium hydrogen sulfate, 4-acetyl-1-benzylpyridinium p-toluene sulfonate, 4-acetyl-1-benzylpyridinium benzene sulfonate, 4-acetyl-1-benzylpyridinium bromide, 4-acetyl-1-benzylpyridinium hydrogen sulfate, 4-acetyl-1-(2-methoxyethyl)pyridinium p-toluene sulfonate, 4-acetyl-1-(2-methoxyethyl)pyridinium benzene sulfonate, 4-acetyl-1-(2-methoxyethyl)pyridinium bromide or 4-acetyl-1-(2-methoxyethyl)pyridinium hydrogen sulfate as well as N-methyl-3,4-dihydroisoquinolinium p-toluene sulfonate, N-methyl-3,4-dihydroisoquinolinium benzene sulfonate, N-methyl-3,4-dihydroisoquinolinium hydrogen sulfate, N-allyl-3,4-dihydroisoquinolinium p-toluene sulfonate, N-allyl-3,4-dihydroisoquinolinium benzene sulfonate, N-allyl-3,4-dihydroisoquinolinium bromide, N-allyl-3,4-dihydroisoquinolinium acetate, 3,4-dihydro-2-(3-hydroxypropyl)isoquinolinium p-toluene sulfonate, 3,4-dihydro-2-(3-hydroxypropyl)isoquinolinium benzene sulfonate, 3,4-dihydro-2-(3-hydroxypropyl)isoquinolinium bromide, 3,4-dihydro-2-(3-hydroxypropyl)isoquinolinium acetate, 3,4-dihydro-2-(2-hydroxyethyl)isoquinolinium p-toluene sulfonate, 3,4-dihydro-2-(2-hydroxyethyl)isoquinolinium benzene sulfonate, 3,4-dihydro-2-(2-hydroxyethyl)isoquinolinium bromide or 3,4-dihydro-2-(2-hydroxyethyl)isoquinolinium acetate.

Bleach boosters used in addition to or instead of peroxy compounds are preferably present in cosmetic agents according to the invention in amounts of 0.5 to 30% by weight, particularly 2 to 20% by weight, based on total weight of the ready for use agent.

In order to increase the lightening power, at least one optionally hydrated $SiO_2$ compound can be added as the bleach booster. Although small amounts of the optionally hydrated $SiO_2$ compounds already increase the lightening power, according to the invention it may be preferred to use the optionally hydrated $SiO_2$ compounds in amounts of 0.05% to 15% by weight, particularly preferably in amounts of 0.15% to 10% by weight and quite particularly preferably in amounts of 0.2% to 5% by weight, based on the anhydrous agent according to the invention. The quantitative data here in each case give the content of $SiO_2$ compounds (without their water fraction) in the agents. Regarding the optionally hydrated $SiO_2$ compounds, the present invention is not subject to any limitations. Preference is given to silicic acids, their oligomers and polymers, and their salts. Preferred salts are alkali metal salts, in particular, the potassium and sodium salts. Sodium salts are quite particularly preferred. The optionally hydrated $SiO_2$ compounds can be present in various forms. According to the invention, $SiO_2$ compounds are preferably used in the form of silica gels or particularly preferably as water glass. Some of these $SiO_2$ compounds may be in the form of an aqueous solution. According to the invention, quite particular preference is given to water-glasses formed from a silicate of Formula $(SiO_2)_n(Na_2O)_m(K_2O)_p$, where n is a positive rational number and m and p, independently of one another, are a positive rational number or are 0, with the provisos that at least one of the parameters m or p is different from 0 and the ratio between n and the sum of m and p is between 1:4 and 4:1. Metasilicates can preferably be employed, particularly those in the above Formula which are characterized by the ratio between n and the sum of m and p being less than 1 and which can be considered as chain-like polymeric structures of the anion $[SiO_3]^{2-}$. Sodium metasilicate of the Formula $[NaSiO_3]_x$ is particularly preferred. Particularly preferred water glasses according to the invention are sold, inter alia, by Henkel under the names Ferrosil® 119, Natronwasserglas 40/42, Portil® A, Portil® AW and Portil® W, and by Akzo under the name Britesil® C20.

Although in principle there is no limitation with respect to the formulation of blonding preparation (C), it has proved to be inventively preferred when preparation (C) is an anhydrous formulation. In the context of the present invention, anhydrous means a water content, based on preparation (C), of 5 wt. % or less, especially 2 wt. % or less. Blonding preparations having 0.1 wt. % or less water can be inventively quite particularly preferred.

Preparation (C) is preferably formulated as a powder or an anhydrous paste. When the formulation is an anhydrous paste, it has proven particularly preferable when preparation (C) has at least one non-hydroxylated fatty acid ester with a melting point of maximum 50° C., particularly a maximum of 30° C., and/or at least one $C_{10}$-$C_{30}$ fatty acid containing at least one additional hydroxyl group and/or a derivative thereof.

Esters of non-hydroxylated $C_6$-$C_{30}$ alkyl monocarboxylic acids with $C_2$-$C_{30}$ monohydric alcohols are inventively suitable as the fatty acid ester. Monoesters of fatty acids with monoalcohols having 2 to 24 carbon atoms are preferred. According to the invention, isopropyl myristate (Rilanit® IPM), isononanoic acid $C_{16-18}$ alkyl ester (Cetiol® SN), 2-ethylhexyl palmitate (Cegesoft® 24), stearic acid 2-ethylhexyl ester (Cetiol® 868), cetyl oleate, cocofatty alcohol caprinate/-caprylate (Cetiol® LC), n-butyl stearate, oleyl erucate (Cetiol® J 600), isopropyl palmitate (Rilanit® IPP), oleyl oleate (Cetiol®), lauric acid hexyl ester (Cetiol® A), myristyl myristate (Cetiol® MM), cetearyl isononanoate (Cetiol® SN), oleic acid decyl ester (Cetiol® V) are particularly preferred.

The above executions for the first and second subject matters of the invention are valid in regard to the preferred embodiments for preparation (A) and oxidizing agent preparation (B).

A particularly preferred presentation form of the agent is a kit-of-parts having in containers separate from each other at least one oxidizing agent preparation (B) having at least one oxidizing agent chosen from hydrogen peroxide and its addition compounds on solid carriers, at least one blonding preparation (C) having at least one bleach booster, and at least one preparation (A), wherein preparation (A) has in a cosmetic carrier at least one non-ionic component having an HLB value of 8.0 or less and a combination of at least one blue substantive dye and one red substantive dye, wherein the value of the weight ratio between the sum of all blue substantive dyes and the sum of all red substantive dyes is greater than or equal to 1.

The above executions are valid in regard to the preferred embodiments for preparation (A), oxidizing agent preparation (B) and blonding preparation (C).

The mixture of preparations (A) and (B) or optionally of preparations (A), (B) and (C) prior to application results in an application mixture according to the invention.

Oxidizing agent preparation (B) and/or preparation (A) that comprises the matting dyes are preferably made up as five-flowing preparations. An emulsifier or a surfactant is preferably added to free-flowing preparations (A) and/or (B), wherein surface active substances are designated as surfactants or as emulsifiers depending on their field of application, and are chosen from anionic, cationic, zwitterionic, amphoteric and non-ionic surfactants and emulsifiers.

Suitable anionic surfactants for the inventive preparations include all anionic surface-active materials suitable for use on the human body. Preferred anionic surfactants are alkyl sulfates, alkyl ether sulfates and ether carboxylic acids containing 10 to 18 carbon atoms in the alkyl group and up to 12 glycol ether groups in the molecule. Suitable zwitterionic emulsifiers are betaines such as N-alkyl-N,N-dimethylammonium glycinates, N-acyl-aminopropyl-N,N-dimethylammonium glycinates and 2-alkyl-3-carboxymethyl-3-hydroxyethyl-imidazolines, each having 8 to 18 carbon atoms in the alkyl or acyl group, as well as cocoacylaminoethylhydroxyethylcarboxymethyl glycinate. A preferred zwitterionic surfactant is known under the INCI name Cocamidopropyl Betaine. Examples of suitable ampholytic surfactants are N-alkylglycines, N-alkylamino propionic acids, N-alkylamino butyric acids, N-alkylimino dipropionic acids, N-hydroxyethyl-N-alkylamidopropylglycine, N-alkyltaurines, N-alkylsarcosines, 2-alkylamino propionic acids and alkylamino acetic acids, each with about 8 to 24 carbon atoms in the alkyl group. Particularly preferred amphoteric surfactants are N-cocoalkylamino propionate, the cocoacylaminoethylamino propionate and the $C_{12-18}$ acyl sarcosine. Furthermore, it has proven advantageous when the lighteners according to the invention comprise additional non-ionic, surface-active substances that do not fall under the above described category of non-ionic components having an HLB value of 8.0 or less. The $C_8$-$C_{22}$ alkyl mono- and oligo-glycosides and their ethoxylated analogs are particularly suitable as the non-ionic surfactants. In particular, the non-ethoxylated compounds have proven to be particularly suitable. Alkylene oxide addition products on saturated, linear fatty alcohols and fatty acids, each with 2 to 30 moles ethylene oxide per mole fatty alcohol or fatty acid, have proved to be additional preferred non-ionic surfactants. Preparations with excellent properties are also obtained when they include fatty acid esters of ethoxylated glycerin as the non-ionic surfactant. Anionic, non-ionic, zwitterionic or amphoteric surfactants are present in quantities of 0.1-45 wt. %, preferably 1-30 wt. % and quite particularly preferably from 1-15 wt. %, based on total amount of the ready for use agent.

According to the invention, cationic surfactants of the type quaternary ammonium compounds, esterquats and amido amines are likewise preferred. Preferred quaternary ammonium compounds are ammonium halides, especially chlorides and bromides, such as alkyltrimethylammonium chlorides, dialkyldimethylammonium chlorides and trialkylmethylammonium chlorides, as well as imidazolium compounds known under the INCI names Quaternium-27 and Quaternium-83. Long alkyl chains of the abovementioned surfactants preferably contain 10 to 18 carbon atoms. Quaternized protein hydrolyzates represent further inventively usable cationic surfactants. The alkylamido amines are normally manufactured by amidation of natural or synthetic fatty acids and fatty acid fractions with dialkylamino amines (e.g., Tegoamid® S 18: stearamidopropyldimethylamine). Preferred esterquats are quaternized ester salts of fatty acids with triethanolamine, quaternized ester salts of fatty acids with diethanolalkylamines and quaternized ester salts of fatty acids with 1,2-dihydroxypropyldialkylamines. Such products are marketed, for example, under the trade names Stepantex®, Dehyquart® and Armocare®. The products Armocare® VGH-70, an N,N-bis(2-palmitoyloxyethyl)dimethylammonium chloride, as well as Dehyquart® F-75, Dehyquart® C-4046, Dehyquart® L80 and Dehyquart® AU 35 are examples of such esterquats. Agents used according to the invention preferably comprise cationic surfactants in quantities of 0.05 to 10 wt. %, based on total weight of the agent. Quantities of 0.1 to 5 wt. % are preferred.

In a preferred embodiment, non-ionic, zwitterionic and/or amphoteric surfactants as well as mixtures thereof can be used. Preferably, the inventive agents have at least one non-ionic emulsifier with an HLB value of 8 to 18. Non-ionic emulsifiers with an HLB value of 10 to 15 can be particularly inventively preferred.

Inventive agents further include all active substances, additives and auxiliaries known for such preparations. Further exemplary active products, auxiliaries and additives include structure-improving active substances (plant extracts, protein hydrolyzates, panthenol, lactic acid, biotin, niacinamide, mono-, di- and oligosaccharides, serine, lysine); silicone oils; phospholipids; vegetal oils; non-ionic polymers; zwitterionic and amphoteric polymers; anionic polymers; cationic polymers (Celquat® H 100, Celquat® L 200; Polymer JR®400; Merquat® 100; Merquat®550; Merquat® 280; Gafquat®734 and Gafquat®755; Luviquat®; quaternized polyvinyl alcohol; Polyquaternium-1, Polyquaternium 2, Polyquaternium-10; Polyquaternium 17, Polyquaternium 18, Polyquaternium-22 and Polyquaternium 27); perfume oils; cyclodextrins; defoamers such as silicones; dyestuffs to color the agent; anti-dandruff active substances; photo protective agents, in particular derivatized benzophenones, cinnamic acid derivatives and triazines; cholesterol; other fats and waxes such as fatty alcohols, beeswax, montan wax and paraffins; fatty acid alkanolamides; swelling and penetration substances such as glycerin, propylene glycol monoethyl ether, carbonates, hydrogen carbonates, guanidines, ureas, and primary, secondary and tertiary phosphates; opacifiers like latex, styrene/PVP copolymers and styrene/acrylamide copolymers; pearlizers; pigments; propellants like propane-butane mixtures, $N_2O$, dimethyl ether, $CO_2$ and air, as well as antioxidants. One skilled in the art selects these additional materials based on the desired properties of the agent. Concerning further optional ingredients and their amounts used, reference is expressly made to relevant handbooks known to one skilled in the art, for example, the monograph by K. Schrader, Grundlagen and Rezepturen der Kosmetika, $2^{nd}$ Ed., Hüthig Buch Verlag, Heidelberg (1989).

Another subject matter of the present application is a method for blonding keratinic fibers, especially human hair, wherein an agent is manufactured by blending at least one oxidizing agent preparation (B) having at least one oxidizing agent chosen from hydrogen peroxide and its addition products on solid carriers, at least one blonding preparation (C) having at least one bleach booster, and at least one preparation (A), wherein preparation (A) has in a cosmetic carrier at least one non-ionic emulsifier having an HLB value of 8.0 or less and a combination of at least one blue substantive dye and one red substantive dye, wherein the value of the weight ratio between the sum of all blue substantive dyes and the sum of all red substantive dyes is greater than or equal to 1, the agent being left in the hair for a period of 2 to 60 minutes, preferably 5 to 45 minutes, and subsequently rinsing the hair with water and/or a conventional shampoo. In the context of this subject matter of the present invention, the above enunciated statements apply accordingly.

Thus, for example, it has proved particularly advantageous when preparations (A) and (B) are aqueous formulations, whereas blonding preparation (C) is an anhydrous formulation. Furthermore, it is inventively preferred that preparation (C) is in powder form.

Finally, another subject matter of the present application is the use of an agent according to one of the abovementioned subject matters of the invention for matting during the lightening and or blonding of keratinic fibers, especially human hair. In the context of this subject matter of the present invention, the above enunciated statements apply accordingly.

The following examples are intended to illustrate the subject matter of the invention in more detail, without limiting it in any way.

EXAMPLES

Unless otherwise stated, the quantities in the examples are understood to be in weight percent.

The following formulations were produced:

1—Matting Agent

| Raw Material | Quantity [wt. %] |
|---|---|
| Dow Corning 193 Fluid | 0.2 |
| Ammonia 25% | 2.0 |
| Synthalen K | 0.04 |
| Cetiol V | 2.30 |
| Lanette N | 14.00 |
| Cetearyl Alcohol | 3.90 |
| Cutina GMS SE | 6.00 |
| Phospholipid EFA | 0.10 |
| Na₄ EDTA powder 87% | 0.80 |
| Monoethanolamine | 5.00 |
| Dye formulation* | 0.053 |
| L-serine | 0.50 |
| Mirapol A-15 | 0.20 |
| Perfume | Qs |
| Water | Ad 100 |

*consisting of tetrabromophenol blue (75.5 wt. %), Acid Red 92 (18.8 wt. %) and HC Yellow No. 13 (5.7 wt. %), each based on the total weight of the dye formulation.

2—Oxidizing Agent Preparation

| Raw Material | Quantity [wt. %] |
|---|---|
| Na benzoate | 0.04 |
| Dipicolinic acid | 0.10 |
| Disodium pyrophosphate | 0.10 |
| Potassium hydroxide 50% | 0.19 |
| 1,2-Propane diol | 1.50 |
| HEDP 60% | 0.25 |
| Paraffinum Liquidum | 0.30 |
| Genamin STAC | 0.39 |
| Cetearyl alcohol | 3.40 |
| Eumulgin B 2 | 1.00 |
| Hydrogen peroxide 50% | 18.20 |
| Water | ad 100 |

3—Bleach Booster Preparation

| Raw Material | Quantity [wt. %] |
|---|---|
| Sodium metasilicate | 4.6 |
| Portil N | 38.0 |
| Rohagit S hv | 0.5 |
| Cekol 50000 | 2.5 |
| Magnesium carbonate | 14.2 |
| Na₂EDTA | 1.0 |
| Gluadin AGP | 0.1 |
| Silica, pyrogenic | 0.5 |
| Potassium persulfate | 20.4 |
| Sodium persulfate | 10.2 |
| Paraffinum Liquidum | 8.0 |

4—Blonding

Immediately prior to the application onto the fibers, 15 g matting agent were blended with 70 g oxidizing agent preparation and 35 g bleach booster preparation. The resulting application preparation was applied onto light brown or medium brown strands in a liquid ratio of 4:1 and left for 45 minutes at 35° C. on the strands. The strands were subsequently thoroughly rinsed with water and dried with a hair dryer.

An excellent lightening was obtained with good color equilibration with light cinder notes without unwanted orange or red shifts.

5—Index of the Utilized Commercial Product

| | |
|---|---|
| Dow Corning ® 193 Fluid | INCI name: PEG-12 Dimethicone (Dow Corning) |
| Synthalen ® K | INCI name: Carbomer (3V Sigma) |
| Cetiol ® V | INCI name: Decyl Oleate (Cognis) |
| Lanette ® N | INCI name: Sodium Cetearyl Sulfate, Cetearyl Alcohol (Cognis) |
| Cutina ® GMS SE | INCI name: Glycerin, Glyceryl Stearate, Potassium Stearate (Cognis) |
| Phospholipid EFA ® | INCI name: Linoleamidopropyl PG-Dimonium Chloride Phosphate (Uniqema) |
| Mirapol ® A-15 | INCI name: Polyquaternium-2 (Rhodia) Genamin ® |
| STAC | INCI name: Steartrimoniumchloride (Clariant) |
| Eumulgin ® B 2 | INCI name: Ceteareth-20 (Cognis) |
| Portil ® N | INCI name: Sodium Silicate (Cognis) |
| Rohagit ® S hv | INCI name: Acrylates Copolymer (Evonik) |
| Cekol ® 50000 | INCI name: Cellulose Gum (Kelco) |
| Gluadin ® AGP | INCI name: hydrolyzed wheat protein (Cognis) |

I claim:

1. Agent comprising in a cosmetic carrier:
   at least one non-ionic emulsifier having an HLB value of 8.0 or less, and
   a combination of at least one blue substantive dye and at least one red substantive dye, wherein the at least one blue substantive dye is at least a compound according to formula (I) and/or one of its physiologically acceptable salts

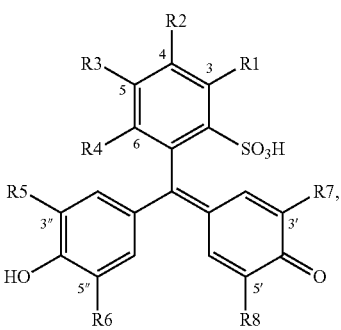

(I)

wherein R1, R2, R3, R4, R5, R6, R7, and R8 are each, independently of one another,
hydrogen, fluorine, chlorine, bromine, iodine, a hydroxyl group or a nitro group,
wherein the at least one red substantive dye is at least a compound according to formula (II) and/or one of its physiologically acceptable salts

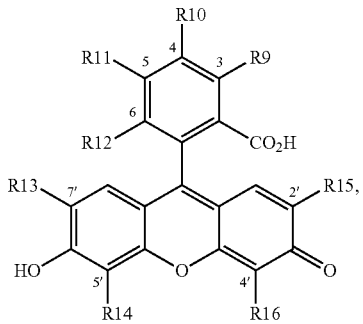

wherein R9, R10, R11, R12, R13, R14, R15 and R16 are each, independently of one another, hydrogen, fluorine, chlorine, bromine, iodine, a hydroxyl group or a nitro group.

wherein the value of the weight ratio between the sum of all blue substantive dyes and the sum of all red substantive dyes is 1 or greater.

2. Agent according to claim 1, wherein the value of the weight ratio between the sum of all blue substantive dyes and the sum of all red substantive dyes is from 1 to 100.

3. Agent according to claim 1 wherein at least one of R1, R2, R3 and/or R4 is fluorine, chlorine, bromine or iodine.

4. Agent according to claim 1 wherein
   a. R1, R2, R3, R4, R5, R6, R7 and R8 are bromine;
   b. R1, R4, R5, R6, R7 and R8 are bromine and R2 and R3 are hydrogen;
   c. R1 and R4 are hydrogen and R2, R3, R5, R6, R7 and R8 are bromine;
   d. R1, R2, R3 and R4 are fluorine and R5, R6, R7 and R8 are bromine;
   e. R1, R2, R3 and R4 are chlorine and R5, R6, R7 and R8 are bromine;
   f. R1, R2, R3 and R4 are iodine and R5, R6, R7 and R8 are bromine;
   g. R1, R2, R3, R4, R5, R6, R7 and R8 are chlorine;
   h. R1, R2, R3 and R4 are bromine and R5, R6, R7 and R8 are chlorine;
   i. R1 and R4 are bromine, R2 and R3 are hydrogen and R5, R6, R7 and R8 are chlorine;
   j. R1 and R4 are hydrogen, R2 and R3 are bromine and R5, R6, R7 and R8 are chlorine;
   k. R1, R2, R3 and R4 stand for iodine and R5, R6, R7 and R8 are chlorine;
   l. R1, R2, R3, R4, R5, R6, R7 and R8 are iodine;
   m. R1, R2, R3 and R4 are fluorine and R5, R6, R7 and R8 are iodine;
   n. R1, R2, R3 and R4 are chlorine and R5, R6, R7 and R8 are iodine; or
   o. R1, R2, R3 and R4 are bromine and R5, R6, R7 and R8 are iodine.

5. Agent according to claim 1 wherein at least one of R9, R10, R11 and/or R12 is hydrogen, chlorine, bromine or iodine.

6. Agent according to claim 1 wherein
   a. R9, R10, R11 and R12 are chlorine and R13, R14, R15 and R16 are bromine;
   b. R9 and R10 are chlorine, R11 and R12 are hydrogen and R13, R14, R15 and R16 are bromine;
   c. R9, R10, R11 and R12 are chlorine and R13, R14, R15 and R16 are iodine;
   d. R9, R10, R11 and R12 are hydrogen and R13, R14, R15 and R16 are bromine; or
   e. R9, R10, R11 and R12 are hydrogen and R13, R14, R15 and R16 are iodine.

7. Agent according to claim 1 wherein the at least one blue substantive dye is at least a compound according to Formula (I) and/or one of its physiologically acceptable salts,

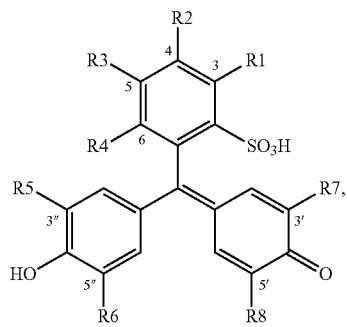

wherein R1, R2, R3, R4, R5, R6, R7 and R8 are bromine, and wherein the at least one red substantive dye is at least a compound according to Formula (II) and/or one of its physiologically acceptable salts,

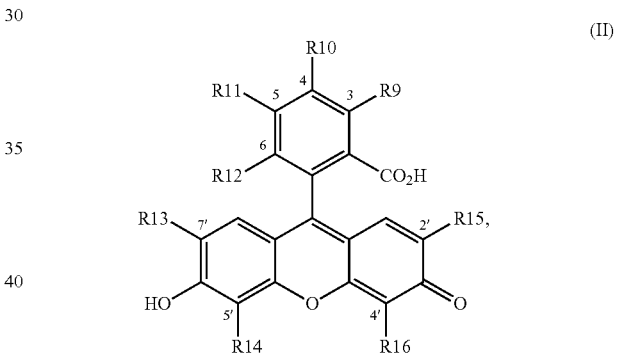

wherein R9, R10, R11 and R12 are chlorine and R13, R14, R15 and R16 are bromine.

8. Agent according to claim 1 wherein the non-ionic component with an HLB value of 8.0 or less is chosen from fatty alcohols, fatty alcohol monoethylene glycol ethers, fatty alcohol diethylene glycol ethers, fatty alcohol triethylene glycol ethers, glycerin monofatty acid esters, glycerin difatty acid esters, glycerin trifatty acid esters, sorbitan monofatty acid esters, sorbitan difatty acid esters, sorbitan trifatty acid esters, pentaerythritol monofatty acid esters, ethylene glycol monofatty acid esters, ethylene glycol difatty acid esters, polyethylene glycol monofatty acid esters, polyethylene glycol difatty acid esters, saccharose monofatty acid esters, saccharose difatty acid esters, propylene glycol monofatty acid esters, fatty acid alkyl esters and combinations thereof.

9. Agent according to claim 1 wherein the non-ionic component with an HLB value of 8.0 or less is at least a fatty alcohol.

10. Method of preparing an agent for bleaching keratinic fibers comprising:
   blending at least one oxidizing agent preparation (B) having at least one oxidizing agent chosen from hydrogen peroxide and its addition products on solid carriers with at least one preparation (A), wherein preparation (A) comprises in a cosmetic carrier at least one non-ionic component having an HLB value of 8.0 or less and a combination of at least one blue substantive dye and one red substantive dye, wherein the at least one blue substantive dye is at least a compound according to formula (I) and/or one of its physiologically acceptable salts

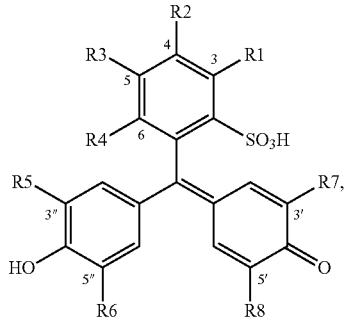

(I)

wherein R1, R2, R3, R4, R5, R6, R7 and R8 are each, independently of one another, hydrogen, fluorine, chlorine, bromine, iodine, a hydroxyl group or a nitro group, wherein the at least one red substantive dye is at least a compound according to formula (II) and/or one of its physiologically acceptable salts

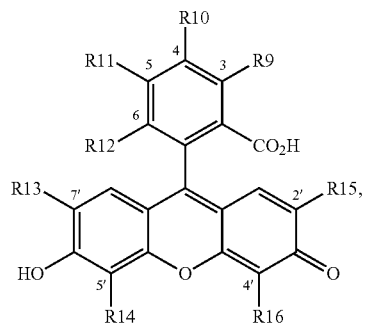

(II)

wherein R9, R10, R11, R12, R13, R14, R15 and R16 are each, independently of one another, hydrogen, fluorine, chlorine, bromine, iodine, a hydroxyl group or a nitro group. wherein the value of the weight ratio between the sum of all blue substantive dyes and the sum of all red substantive dyes is greater than or equal to 1.

11. Method according to claim 10 further comprising blending at least one blonding preparation (C) having at least one bleach booster with preparations (A) and (B).

12. Process for dyeing hair blond comprising:
applying an agent prepared according to claim 10 onto hair,
leaving the agent in the hair for a period of 2 to 60 minutes, and
rinsing the hair with water and/or a conventional shampoo.

* * * * *